US00PP24090P3

(12) United States Plant Patent
Olesen

(10) Patent No.: US PP24,090 P3
(45) Date of Patent: Dec. 17, 2013

(54) MINIATURE ROSE PLANT NAMED 'POULPAH053'

(50) Latin Name: ***Rosa* hybrid**
Varietal Denomination: Poulpah053

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 104 days.

(21) Appl. No.: 13/317,263

(22) Filed: Oct. 13, 2011

(65) Prior Publication Data

US 2013/0097751 P1 Apr. 18, 2013

(51) Int. Cl.
*A01H 5/00* (2006.01)

(52) U.S. Cl.
USPC ..... Plt./122

(58) Field of Classification Search
USPC ..... Plt./122
See application file for complete search history.

(56) References Cited

PUBLICATIONS

GTITM UPOVROM Citation for 'Poulpah053' as per QZ PBR 20100220; Feb. 3, 2010.*

* cited by examiner

*Primary Examiner* — Kent L Bell

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah053'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2006 and the resulting seeds were planted in a controlled environment in Fredensborg, Denmark. The new variety, named 'Poulpah053', originated as a single seedling from the stated cross.

The new variety may be distinguished from its female seed parent primarily by flower color. The female seed parent has pink flowers while the new variety has red flowers.

The new variety may be distinguished from its male pollen parent primarily by flower color. The male parent has medium red flowers while the new variety has red flowers.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah053' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah053' was selected by the inventor as a single plant from the progeny of the hybridization in 2006.

Asexual reproduction of 'Poulpah053' by cuttings and traditional budding was first done by Mogens N. Olesen in the nursery in Fredensborg, Denmark in June 2007. This initial and other subsequent propagations conducted in controlled environments have demonstrated that the characteristics of 'Poulpah053' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah053'.

DETAILED DESCRIPTION OF THE VARIETY

The following is a description of 'Poulpah053', as observed in its growth in glasshouses in Burlington, Ontario, Canada. Observed plants are 3 months of age and were cultivated in 15 cm pots. Color references are made using The Royal Horticultural Society (London, England) Colour Chart, 2001, except where common terms of color are used.

For a comparison, several physical characteristics of the rose variety 'Poulhi021', U.S. Plant Pat. No. 15,853. are compared to 'Poulpah053' in Chart 1.

CHART 1

| | 'Poulpah053' | 'Poulhi021' |
|---|---|---|
| Petalage: | 30 | 43 |
| Flower Diameter: | 45 mm | 50 to 55 mm |
| General Tonality of Flower Color: | Red Group 53B | Red Group 42A to Red Group 53B |

FLOWER AND FLOWER BUD

Blooming habit: Continuous.

Flower bud:

*Size.*—Upon opening, 20 mm in length from base of receptacle to end of bud. 13 mm in diameter.

*Bud form.*—Ovate.

*Bud color.*—As sepals unfold petals are Red Group 53A.

*Sepals.*—Upper Surface: Color: Yellow-Green Group 147A with anthocyanin the color of Greyed-Red Group 178A. Texture: Pubescent. Lower Surface: Color: Green Group 137A with anthocyanin the color of Greyed-Red Group 178A. Texture: Smooth. Shape: Apex: Cirrhose. Base: Flat at union with receptacle. Margins: Margins have moderate foliaceous appendages on three of the five sepals. Size: 25 mm long by 10 mm wide.

*Receptacle.*—Surface Texture: Smooth. Shape: Funnel. Size: 5 mm in height, by 6 mm wide. Color: Yellow-Green Group 144A.

*Pedicel.*—Surface: Somewhat rough with small prickles. Length: On average 40 mm. Diameter: About 3 mm. Color: Yellow-Green Group 144B with strong intonations of Greyed-Red Group 178A. Strength: Medium strength.

*Borne.*—Singly.

Flower bloom:

*Fragrance.*—None.

*Duration.*—As a pot plant, flowers last up to 28 days. Petals do not fall cleanly away from plant.

*Size.*—45 mm flower diameter. 20 mm deep.

*Form.*—Hybrid tea shaped, opening fully to form a rosette with a tightly closed center.

*Shape of flower, side view.*—The upper portion is flattened convex. The lower portion is a flattened convex.

Petalage: There are normally 30 petals, 8 to 10 of which are petaloids.

Color:

*Upon opening, petals.*—Outermost petals: Upper Surface: Red Group 53B. Lower Surface: Red-Purple Group 60A. Innermost petals: Upper Surface: Red Group 53B. Lower Surface: Red-Purple Group 60A. Petal Spots: Yellow Group 11C on upper and lower surface. Outer and inner petals: Upper Surface: Red Group 53B. Lower Surface: Red-Purple Group 60A. Petal Spots: Yellow Group 11C on upper and lower surface.

General tonality: Red Group 53B.

Petals:

*Petal reflex.*—Strong.

*Petal margin.*—Entire and uniform.

*Shape.*—Generally broad elliptic. Base: Rounded. Apex: Rounded.

*Size.*—25 mm long by 30 mm wide on average. Inner petals are 15 mm long by 15 mm wide.

*Thickness.*—Average.

*Texture.*—Smooth.

Petaloids:

*Quantity.*—Normally, there are 8 to 10 petaloids.

*Size.*—15 mm long; 8 mm wide.

*Shape.*—Apex is rounded. Base is acute. Petaloids are partially asymmetrical party asymetrical. The margins are stongly undulated.

*Color.*—Upper Surface: Red Group 53B. Lower Surface: Red-Purple Group 60A. Petal Spots: Yellow Group 11C on upper and lower surface.

Reproductive organs:

*Pollen.*—None observed.

*Anthers.*—Size: 2 mm long. Color: Yellow-Orange Group 16B and Red Group 39A. Quantity: 60 on average.

*Filaments.*—Color: Yellow Group 12A. Length: 4 mm.

*Pistils.*—Length: 5 mm long. Quantity: On average, 40.

*Stigmas.*—Superior relative to the length of the filaments and the height of the anthers. Color: Greyed-Yellow Group 160A.

*Styles.*—Color: Greyed-Yellow 162D.

*Seed formation.*—Not observed.

PLANT

Plant growth: Upright. When grown as a 15 cm pot plant on its own roots, the average height of the plant itself is 17 cm and the average width is 15 cm.

Stems:

*Color.*—Young wood: Yellow-Green Group 144B. Older wood: Yellow-Green Group 144A.

*Internodal distance.*—20 mm on average.

*Length of stems.*—13 cm from the base of the plant to the flowering portion.

*Diameter.*—3 to 4 mm.

*Surface texture.*—Young wood: Smooth. Older wood: Smooth.

Prickles: None observed.

Plant foliage: On average, 5 leaflets.

*Compound leaf size.*—70 mm (l)×55 mm (w).

*Quantity.*—2 leaves per 10 cm of stem.

*Color.*—Juvenile foliage: Upper Leaf Surface: Yellow-Green Group 147A. Lower Leaf Surface: Yellow-Green Group 147B. Anthocyanin: Greyed-Purple 183C underneath and the upper margins. Mature foliage: Upper Leaf Surface: Yellow-Green Group 147A. Lower Leaf Surface: Yellow-Green Group 147B.

Plant leaves and leaflets:

*Stipules.*—Size: 9 mm in length. Shape: Linear, slightly broad based with outward extending apecies. Margins: Entire. Color: Yellow-Green Group 147A.

*Petiole.*—Length: 10 mm on average. Diameter: 1 mm. Color: Upper surface is Green Group 138A. Anthocyanin is the color of Greyed-Purple Group 183A. The lower surface is Yellow-Green Group 144B. Underneath: Small prickles observed.

*Rachis.*—Length: About 20 mm. Color: Upper surface is Green Group 138A. Anthocyanin is the color of Greyed-Purple Group 183A. The lower surface is Yellow-Green Group 144B. Underneath: Small prickles observed.

*Leaflet.*—Size: 55 mm in length by 30 mm wide. Margin: Serrate. General Shape: Elliptical. Apex Shape: Acute. Base Shape: Round to acute. Texture: Smooth.

Arrangement: Odd pinnate. Venation: Reticulate. Leaf Gloss: Matte surface.

Disease resistance: Average resistance to powdery and downy mildew, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticultural Society heat zone 7.

What is claimed is:

1. A new and distinct variety of rose plant of the miniature class named 'Poulpah053', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

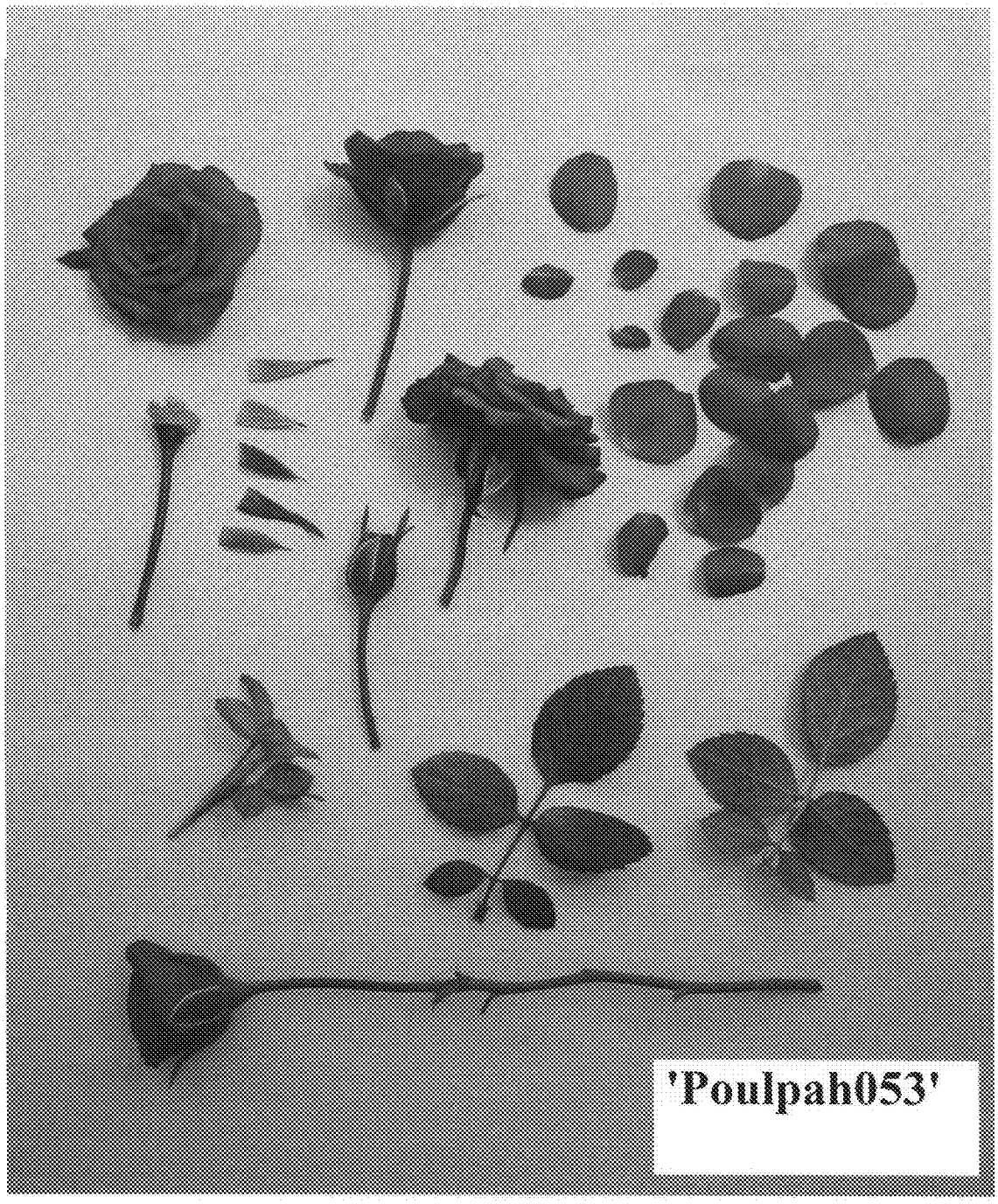
'Poulpah053'